US012616762B2

(12) United States Patent
    Madhav et al.

(10) Patent No.: US 12,616,762 B2
(45) Date of Patent: May 5, 2026

(54) ULTRAVIOLET DEVICE AND METHODS OF USING THE SAME

(71) Applicant: The Boeing Company, Chicago, IL (US)

(72) Inventors: Jagdish T. Madhav, Bothell, WA (US); Geoffrey Thomas Warr, Kent, WA (US)

(73) Assignee: The Boeing Company, Arlington, VA (US)

( * ) Notice: Subject to any disclaimer, the term of this patent is extended or adjusted under 35 U.S.C. 154(b) by 1227 days.

(21) Appl. No.: 17/511,365

(22) Filed: Oct. 26, 2021

(65) Prior Publication Data
    US 2022/0211889 A1     Jul. 7, 2022

Related U.S. Application Data

(60) Provisional application No. 63/134,110, filed on Jan. 5, 2021.

(51) Int. Cl.
    *G01N 21/00*     (2006.01)
    *A61L 2/10*     (2006.01)
    *A61N 5/00*     (2006.01)
    *B64F 5/30*     (2017.01)
    *G05F 1/00*     (2006.01)

(52) U.S. Cl.
    CPC ................... *A61L 2/10* (2013.01); *B64F 5/30* (2017.01); *A61L 2202/11* (2013.01); *A61L 2202/25* (2013.01)

(58) Field of Classification Search
    CPC .... A61L 2202/11; A61L 2202/25; A61L 2/10; B64F 5/30; H05B 37/02

USPC ......... 250/504 R, 494, 492.1; 128/371–372; 422/24; 315/292

See application file for complete search history.

(56) References Cited

U.S. PATENT DOCUMENTS

| | | | |
|---|---|---|---|
| 2,423,884 A | 7/1947 | Glass |
| 2,569,772 A | 10/1951 | Olsen |

(Continued)

FOREIGN PATENT DOCUMENTS

| | | |
|---|---|---|
| EP | 3068133 A1 | 9/2016 |
| EP | 3929084 A1 | 12/2021 |

(Continued)

OTHER PUBLICATIONS

European Patent Office, Office Action Issued in Application No. 21204470.5, Oct. 8, 2024, 5 pages.

(Continued)

*Primary Examiner* — Monzer R Chorbaji
(74) *Attorney, Agent, or Firm* — Alleman Hall LLP

(57) ABSTRACT

A device including an outer shell having a first longitudinal axis and a first arcuate shape. The outer shell is opaque to ultraviolet light and to visible light. The device also includes an inner shell having a second longitudinal axis. The inner shell is connected longitudinally to the outer shell along a first longitudinal length and a second longitudinal length. The inner shell has a second arcuate shape different than the first arcuate shape. A chamber is disposed between the outer shell and the inner shell. The chamber is defined by a difference between the first arcuate shape and the second arcuate shape. The device also includes an ultraviolet light source disposed along the second longitudinal axis.

7 Claims, 8 Drawing Sheets

(56) References Cited

U.S. PATENT DOCUMENTS

| | | | | |
|---|---|---|---|---|
| 4,309,616 | A * | 1/1982 | Wolff | A61N 5/0614 |
| | | | | 250/504 R |
| 9,493,112 | B2 | 11/2016 | Thomas et al. | |
| 9,555,882 | B2 | 1/2017 | Tanielian | |
| 10,696,404 | B1 | 6/2020 | Madhav et al. | |
| 2007/0053188 | A1* | 3/2007 | New | B60Q 3/43 |
| | | | | 362/276 |
| 2013/0200818 | A1* | 8/2013 | Cercone | H05B 45/3578 |
| | | | | 362/372 |
| 2016/0325836 | A1 | 11/2016 | Teo | |
| 2017/0100500 | A1 | 4/2017 | Garner et al. | |
| 2021/0323699 | A1* | 10/2021 | Myers | B64F 5/30 |

FOREIGN PATENT DOCUMENTS

| | | | |
|---|---|---|---|
| EP | 3929085 | A1 | 12/2021 |
| KR | 20070059937 | A1 | 6/2007 |

OTHER PUBLICATIONS

Office Action pursuant to Article 94(3) EPC in related European Patent Application No. 21204470.5 dated Jun. 9, 2023 (7 pages).
Extended European Search Report in related European Patent Application No. 21204470.5 dated Jun. 17, 2022 (12 pages).

* cited by examiner

START

300 — EMIT ULTRAVIOLET LIGHT FROM THE CORRESPONDING ULTRAVIOLET LAMP

302 — ROTATE, CONCURRENTLY, THE CORRESPONDING ROTATING REFLECTOR

304 — USING THE NEGATIVE PRESSURE SOURCE, DRAW AIR FROM THE PASSENGER CABIN, THROUGH THE HOLES, AND INTO THE CORRESPONDING CHAMBER TOWARDS THE NEGATIVE PRESSURE SOURCE

END

1100

1200

ULTRAVIOLET DEVICE AND METHODS OF USING THE SAME

RELATED APPLICATIONS

This application claims priority to U.S. Provisional Patent Application 63/134,110, filed Jan. 5, 2021, the entirety of which is hereby incorporated by reference.

BACKGROUND

Improved anti-viral and sterilization devices and methods are sought. Ultraviolet light is one means for sterilizing a surface or an area of viruses. As used herein, the term "UV" means "ultraviolet" and the term "emitter" refers to a UV lamp or other UV light source.

SUMMARY

The one or more embodiments provide for a device. The device includes an outer shell having a first longitudinal axis and a first arcuate shape. The outer shell is opaque to ultraviolet light and to visible light. The device also includes an inner shell having a second longitudinal axis. The inner shell is connected longitudinally to the outer shell along a first longitudinal length and a second longitudinal length. The inner shell has a second arcuate shape different than the first arcuate shape. A chamber is disposed between the outer shell and the inner shell. The chamber is defined by a difference between the first arcuate shape and the second arcuate shape. The device also includes an ultraviolet light source disposed along the second longitudinal axis.

The one or more embodiments also provide for a vehicle. The vehicle includes a fuselage including an outer skin. The fuselage has an interior including a passenger cabin and a utility space defined between the outer skin and the passenger cabin. The passenger cabin and the utility space are separated by a ceiling. The ceiling is of varying height relative to a floor of the passenger cabin. The ceiling includes an inset area, and storage bins connected to the ceiling extend into the passenger cabin, relative to the inset area. The vehicle also includes devices connected to the ceiling within the inset area. Each of the devices includes a corresponding rotating reflector disposed around a corresponding ultraviolet lamp that is fixed relative to the fuselage. The devices are arranged in series longitudinally end-to-end.

The one or more embodiments also provide for a method of sterilizing a vehicle. The vehicle includes a fuselage including an outer skin. The fuselage has an interior including a passenger cabin and a utility space defined between the outer skin and the passenger cabin. The passenger cabin and the utility space are separated by a ceiling. The ceiling is of varying height relative to a floor of the passenger cabin. The ceiling includes an inset area. Storage bins are connected to the ceiling extend into the passenger cabin, relative to the inset area. Devices are connected to the ceiling within the inset area. Each of the devices includes a corresponding rotating reflector disposed around a corresponding ultraviolet lamp that is fixed relative to the fuselage. The devices are arranged in series longitudinally end-to-end. The method includes emitting ultraviolet light from the corresponding ultraviolet lamp. The method also includes concurrently rotating the corresponding rotating reflector.

Other aspects of the one or more embodiments will be apparent from the following description and the appended claims.

DETAILED DESCRIPTION

Figure 1:
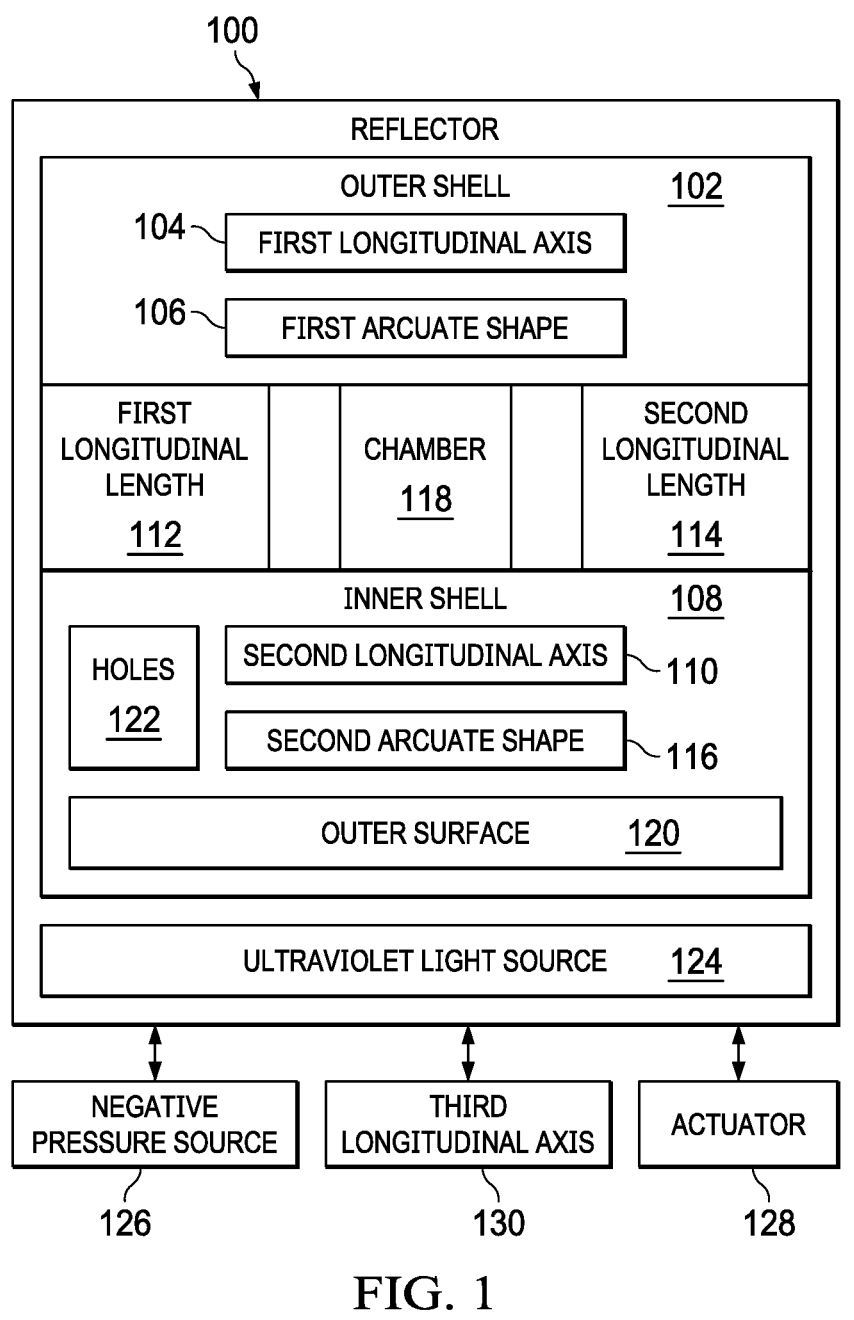
FIG. 1 shows a block diagram of a reflector, in accordance with one or more embodiments.

Specific embodiments of the one or more embodiments will now be described in detail with reference to the accompanying figures. Like elements in the various figures are denoted by like reference numerals for consistency.

In the following detailed description of the embodiments, numerous specific details are set forth in order to provide a more thorough understanding of the one or more embodiments. However, it will be apparent to one of ordinary skill in the art that the one or more embodiments may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

The term "about," when used with respect to a physical property that may be measured, refers to an engineering tolerance anticipated or determined by an engineer or manufacturing technician of ordinary skill in the art. The exact quantified degree of an engineering tolerance depends on the product being produced and the technical property being measured. For a non-limiting example, two angles may be "about congruent" if the values of the two angles are within ten percent of each other. However, if an engineer determines that the engineering tolerance for a particular product should be tighter, then "about congruent" could be two angles having values that are within one percent of each other. Likewise, engineering tolerances could be loosened in other embodiments, such that "about congruent" angles have values within twenty percent of each other. In any case, the ordinary artisan is capable of assessing what is an acceptable engineering tolerance for a particular product, and thus is capable of assessing how to determine the variance of measurement contemplated by the term "about."

As used herein, the term "connected to" contemplates at least two meanings. In a first meaning, unless otherwise stated, "connected to" means that component A was, at least at some point, separate from component B, but then was later joined to component B in either a fixed or a removably attached arrangement. In a second meaning, unless otherwise stated, "connected to" means that component A could have been integrally formed with component B. Thus, for example, assume a bottom of a pan is "connected to" a wall of the pan. The term "connected to" may be interpreted as the bottom and the wall being separate components that are snapped together, welded, or are otherwise fixedly or removably attached to each other. Additionally, the term "connected to" also may be interpreted as the bottom and the wall being contiguously together as a monocoque body formed by, for example, a molding process. In other words, the bottom and the wall, in being "connected to" each other, could be separate components that are brought together and joined, or may be a single piece of material that is bent at an angle so that the bottom panel and the wall panel are identifiable parts of the single piece of material.

In general, the one or more embodiments relate to devices and methods for sterilizing vehicles using ultraviolet light. While ultraviolet light is, by itself, an efficient means for sterilizing viruses, vehicles can be challenging environments in which to use ultraviolet light for such sterilization. Vehicles have many nooks, crannies and objects within them for use by passengers and crew. Examples of such objects that can create shadows are overhead luggage bins, chairs, door handles, etc. Due to shadows created by the nooks, crannies, and objects, many areas of the vehicle may not receive a sufficient flux of ultraviolet light to achieve a desired degree of viral sterilization.

The one or more embodiments address this and other technical issues by providing an ultraviolet lamp that is configured to maximize the desired ultraviolet flux coverage in a vehicle. The ultraviolet lamp of the one or more embodiments may also include a vacuum system to remove ozone naturally produced by an ultraviolet light source. The ultraviolet lamp may include one or more additional ultraviolet light sources disposed in the vehicle to provide a desired ultraviolet flux coverage in the vehicle.

The following definitions apply throughout the description. The term "flux" is defined as a measurable amount of light on or in a defined physical area per unit of time. The term "ultraviolet" light is defined as light with a wavelength in the range of about 10 nanometers to about 400 nanometers. In an embodiment, the range may be limited from about 100 nanometers to about 400 nanometers. In a specific embodiment, the ultraviolet light emitted is at about 222 nanometers.

Attention is now turned to the figures. FIG. 1 shows a block diagram of a reflector, in accordance with one or more embodiments. Specific examples of the reflector (100) shown in FIG. 1 are shown in FIG. 5 through FIG. 10. The device shown in FIG. 1 may be characterized as a vehicle sanitation device in some embodiments.

The reflector (100) includes an outer shell (102). The outer shell (102) is a material that is opaque to ultraviolet light and to visible light. Examples of materials for the outer shell (102) may include composite materials and metals.

The outer shell (102) is defined by a first longitudinal axis (104). The first longitudinal axis (104) is a reference axis. The first longitudinal axis (104) is used to define a length of the outer shell (102), and may be used to define or reference an axis of rotation of the outer shell (102), as described further below.

The outer shell (102) is also defined by a first arcuate shape (106). The first arcuate shape (106) is a curve defined radially with respect to the first longitudinal axis (104). For example, the first arcuate shape (106) may be partially circular, but may have a complex shape of curves. As used herein, the term "arcuate" contemplates one or more corners, and thus "arcuate" does not necessarily imply a smooth shape. In any case, the first arcuate shape (106) is open along at least over an arc defined by a radius from the first longitudinal axis (104). Specific examples of arcuate shapes that could be used are elliptical or parabolic.

The outer shell (102) may have a decorative finish that matches the cabin on the outside of the outer shell (102). The outer shell (102) may, in some embodiments, be reflective on the inside. However, as discussed below, typically the inner shell (108) is reflective, particularly to ultraviolet light.

The reflector (100) also includes an inner shell (108). As mentioned above, the inner shell (108) is composed of a material that is, at least on one side of the inner shell (108), reflective to ultraviolet light. For example, the inner shell (108) may be formed from aluminum, with a reflective coating facing the lamp side, or some other reflective metal. Materials other than metals may be used, so long as the material in the finished form is reflective to ultraviolet light (e.g., certain types of glass, polycarbonate materials, etc., with a mirror gloss finish).

As used herein, "reflective" means that the inner shell (108) reflects more ultraviolet light than the inner shell (108) absorbs and scatters. In an embodiment, the inner shell (108) may be "mirror-like". As used herein, "mirror-like" means that at least 85% incident ultraviolet light is reflected from the reflective surface of the inner shell (108).

The inner shell (108) has a second longitudinal axis (110). The second longitudinal axis (110) may be along the same direction or a different direction than the first longitudinal axis (104). In an embodiment, the first longitudinal axis (104) is coincidental with the second longitudinal axis (110), though in an embodiment the first longitudinal axis (104) is at least parallel to the second longitudinal axis (110). The second longitudinal axis (110) is a reference axis that, in the example of FIG. 1 extends out of and into the page. The second longitudinal axis (110) is used to define a length of the inner shell (108), and may be used to define or reference an axis of rotation of the inner shell (108), as described further below.

The inner shell (108) is connected longitudinally to the outer shell (102) along a first longitudinal length (112) and a second longitudinal length (114). For example, first longitudinally extending edges of the outer shell (102) may connect to second longitudinally extending edges of the inner shell (108). In this manner, the outer shell (102) and the inner shell (108) together form a housing. The connection may be joining two pieces together, or the housing may be a monocoque structure.

The inner shell (108) is also defined by a second arcuate shape (116). The second arcuate shape (116) is a curve defined radially with respect to the second longitudinal axis (110). For example, the second arcuate shape (116) may be an ellipse, a parabola, or have a complex shape of curves. As used herein, the term "arcuate" contemplates one or more corners, and thus "arcuate" does not necessarily imply a smooth shape. In any case, the second arcuate shape (116) is open along at least over an arc defined by a radius from the second longitudinal axis (110).

Figures 6, 7:
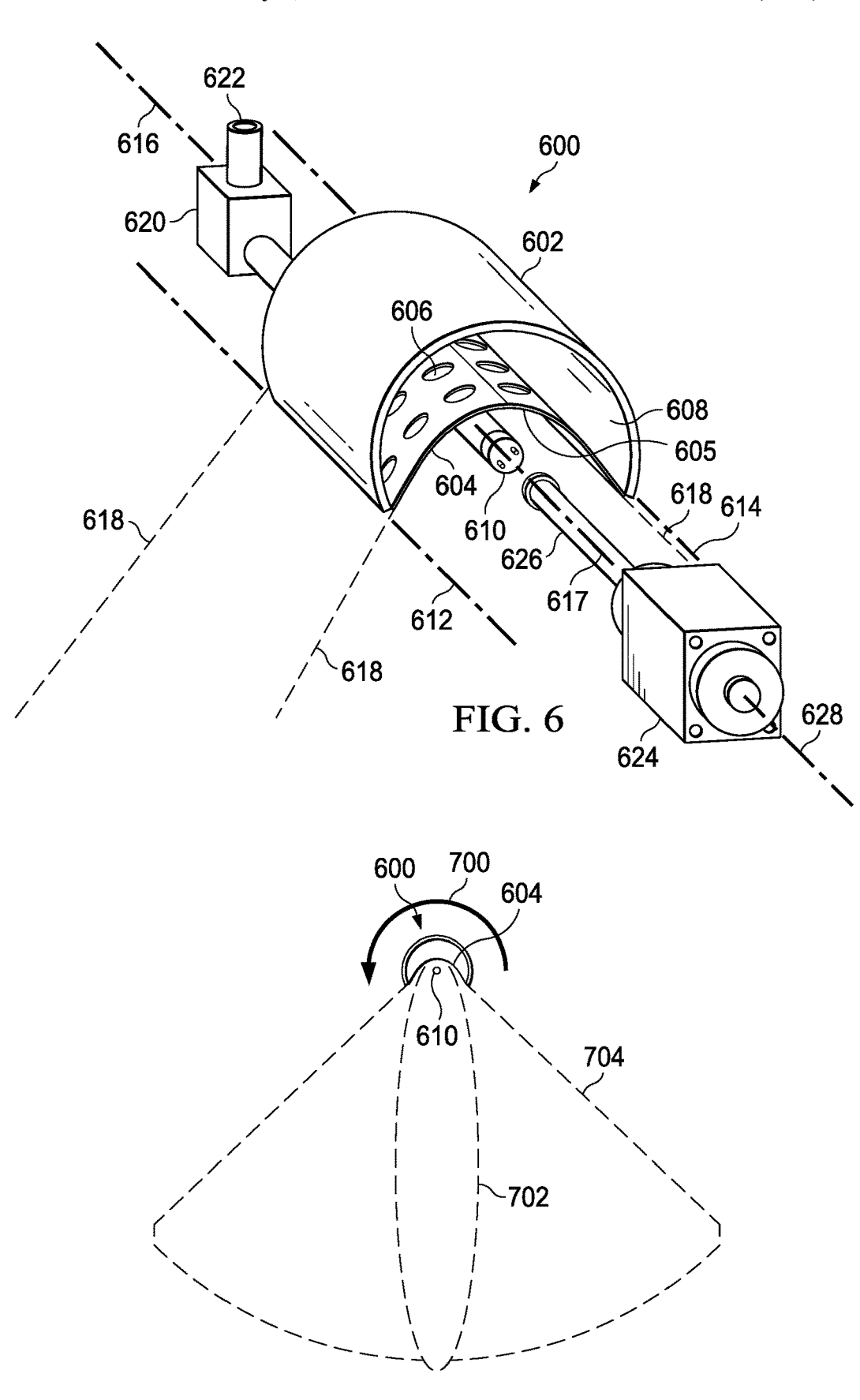
FIG. 6, FIG. 7, FIG. 8, and FIG. 9 show details of a rotatable ultraviolet lamp, in accordance with one or more embodiments.

In an embodiment, the second arcuate shape (116) is different than the first arcuate shape (106). In this manner, a chamber (118) is disposed between the outer shell (102) and the inner shell (108). The shape of the chamber is defined by a difference between first arcuate shape (106) and the second arcuate shape (116). An example of the chamber (118) is shown in FIG. 6.

The inner shell (108) has an outer surface (120). The outer surface (120) is defined as "outer" because the outer surface (120) faces towards ultraviolet light source. The outer surface (120) may also be characterized as pointing away from the reflector (100) and being the surface that is outside of a second surface (not shown) that faces towards the chamber (118) and the outer shell (102). The outer surface (120) reflects ultraviolet light. In an embodiment, the outer surface (120) has a mirror-like reflectivity with respect to ultraviolet light.

The inner shell (108) may include holes (122). The holes (122) are defined as one or more holes that penetrate through the material of inner shell (108). In an embodiment, the holes (122) include many such holes. The holes (122) allow air to be draw from outside the reflector (100) and into the chamber (118), as described further below.

The reflector (100) may also include a ultraviolet light source (124). The ultraviolet light source (124) may be referred to as a "corresponding ultraviolet light source" when multiple such sources are present and any one of the sources is to be considered. The ultraviolet light source (124) is a lamp, light emitting diode (LED), or some other device capable of emitting ultraviolet light. The ultraviolet light source (124) is disposed along the second longitudinal axis (110), along some or all of the length of the inner shell (108). In an embodiment, the ultraviolet light source (124) takes the form of a tube that extends a substantial portion of the length of the inner shell (108) along the second longitudinal axis (110). The term "substantial" means 75% or more of the total length of the inner shell (108), in this particular instance. In a specific embodiment, the ultraviolet light source (124) is a ultraviolet lamp that emits a wavelength of light equal to 222 nm.

The ultraviolet light source (124) may be fixed in its relationship to the inner shell (108). However, in other embodiments, the ultraviolet light source (124) may be movable with respect to the inner shell (108), if desired.

In an embodiment, the ultraviolet light source (124) may be situated at a focal distance from the outer surface (120) of the inner shell (108), such as for the case when the second arcuate shape (116) is an ellipse. Note that in other embodiments the second arcuate shape (116) may be parabolic or have other shapes. In each case, the ultraviolet light source (124) may be situated at the focal distance, as indicated above, but in still other embodiments the ultraviolet light source (124) may be located at points other than the focal distance.

The device shown in FIG. 1 may be varied or may include additional components. For example, the device shown in FIG. 1 may also include a negative pressure source (126) that is in fluid communication with the chamber (118). The negative pressure source (126) may be a vacuum pump, a fan or other blower, or some other device for drawing gasses (e.g., air and ozone) towards the negative pressure source (126).

In another embodiment, the first arcuate shape (106) of the outer shell (102) may be circular or partially circular, and the second arcuate shape (116) of the inner shell (108) may be elliptical or parabolic or partially elliptical or parabolic.

In this case, the difference in arcuate shapes forms the chamber (118) such that a cross-section of the chamber (118) has a crescent shape.

The device shown in FIG. 1 may also include an actuator (128). The actuator (128) may be referred to as a "corresponding actuator" when multiple actuators are present and any one of the actuators is to be considered. The actuator (128) is a mechanical or electromechanical device or set of devices connected to one of the outer shell (102) and/or the inner shell (108) in a manner to rotate the reflector (100). For example, the actuator (128) could take the form of an electrical motor configured to impart torque to a rod connected to the reflector (100). The rod serves as a drive axle that rotates the reflector (100) as the electrical motor rotates the rod.

However, many different types of actuators are contemplated by the actuator (128), and thus the example should not be considered the only embodiment of the actuator (128). In any case, the actuator (128) is configured to rotate the outer shell (102) and the inner shell (108) together about a third longitudinal axis (130). The third longitudinal axis (130) is parallel to the first longitudinal axis (104) and the second longitudinal axis (110). In an embodiment, the three axes (the first longitudinal axis (104), the second longitudinal axis (110), and the third longitudinal axis (130)) are all collinear (i.e. along the single line). However, the three axes could be along one or more different lines in other embodiments. In any case, the three axes are named separately in order to clearly identify different parts or operational parameters of the reflector (100).

For example, a combined assembly of the outer shell (102) and the inner shell (108) is connected to the actuator (128). The actuator (128) is configured to rotate around the ultraviolet light source (124) (which may also be characterized as an ultraviolet lamp) about the third longitudinal axis (130), parallel to the second longitudinal axis (110).

The actuator (128) is configured to rotate the reflector (100) (or just the inner shell (108)) through an angle. In an example, the angle is at least 360 degrees. In other words, the inner shell (108) may be configured to rotate in a manner to reflect ultraviolet light from the ultraviolet light source (124) in all directions around the reflector (100) as the inner shell (108) is rotated by the actuator (128). The actuator (128) may be capable of continuously rotating the inner shell (108), or may rotate the inner shell (108) back and forth over time.

Figure 2:
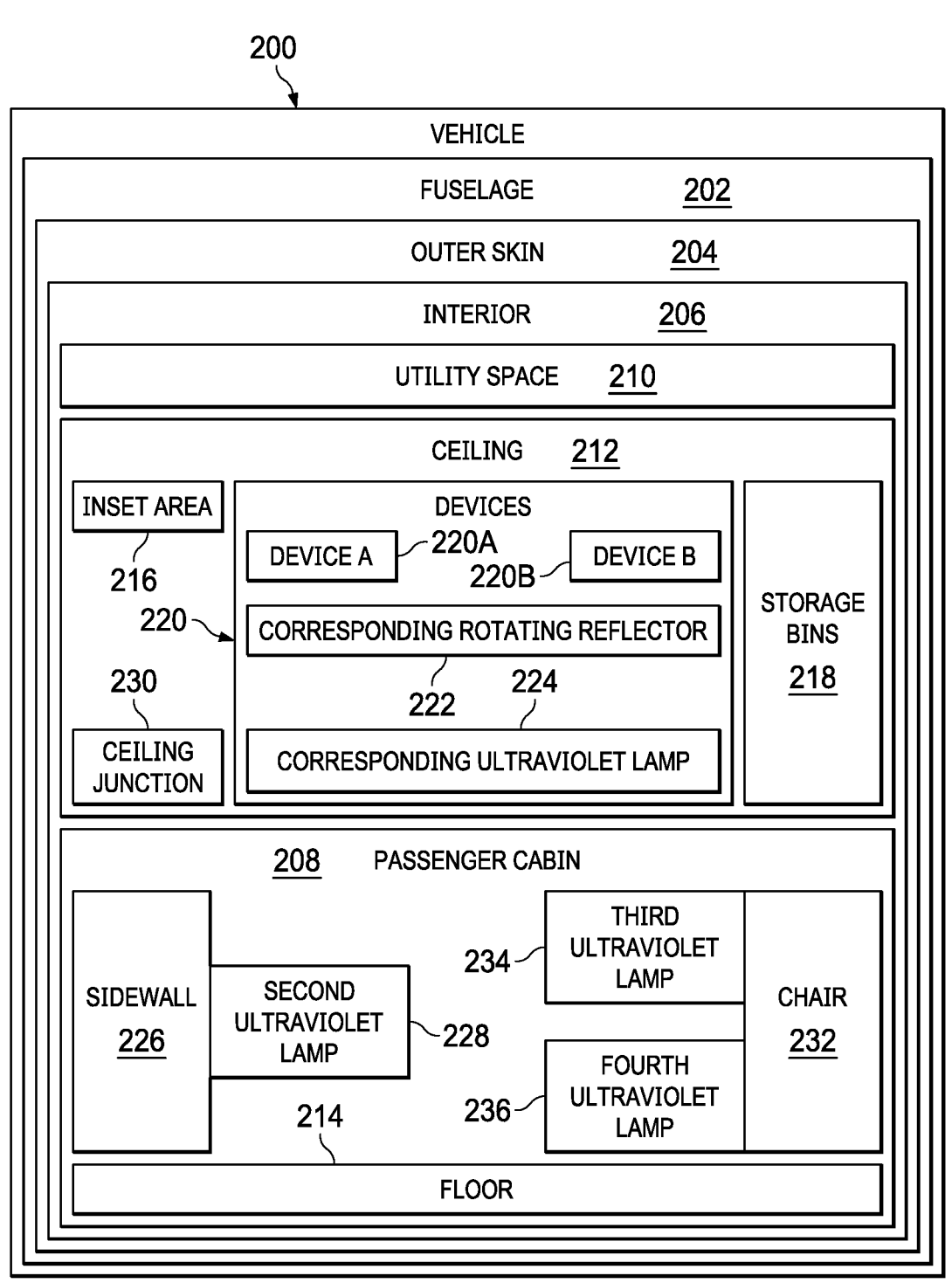
FIG. 2 shows a block diagram of a vehicle, in accordance with one or more embodiments.

Attention is now turned to FIG. 2. FIG. 2 shows a block diagram of a vehicle, in accordance with one or more embodiments. FIG. 2 is an example of the reflector (100) of FIG. 1 installed in a vehicle, such as an aircraft, automobile, ship, etc. Thus, FIG. 2 is a specific example of one possible use of the reflector (100); however, the reflector (100) of FIG. 1 could be used in many different vehicles, in buildings, or elsewhere. Thus, the example of FIG. 2 does not necessarily limit the other embodiments described herein.

The vehicle (200) includes a fuselage (202) that has an outer skin (204). The term "fuselage (202)" ordinarily refers to the superstructure of an aircraft. However, in the context of the example of FIG. 2, the term "fuselage (202)" also contemplates the superstructure of some other type of a vehicle and thus could also be considered a "chassis" or a "hull" or some other term that refers to the superstructure of a vehicle. Thus, for example, the term "fuselage (202)" may refer to the "hull" of a boat or submarine, the "chassis" of a mass transit bus or a train, etc.

The outer skin (204) refers to the portion of the fuselage (202) that composes the outer wall(s) or outer structure(s) of the vehicle (200). Thus, the term "outer skin (204)" refers not only to the thin outer portion of the vehicle (200), but also includes the outer wall(s) or other outer structure(s) of the vehicle (200). In this particular example, the fuselage (202) and the outer skin (204) are primarily formed from composite materials, but may be formed in whole or in part from metal, plastic, or other materials.

The fuselage (202) has an interior (206). The interior (206) is the inside or interior spaces and structures within the outer skin (204). The vehicle (200) includes a passenger cabin (208) and a utility space (210) within the interior (206). The utility space (210) is defined between the interior (206) and the outer skin (204). The passenger cabin (208) is where passengers, which as defined herein also includes vehicle operators such as pilots or drivers, are expected to be located during operation of the vehicle (200). The utility space (210) is a space which is used to contain luggage, equipment, etc., at least partially separate from the passengers.

Thus, for example, the utility space (210) and the passenger cabin (208) could be separated by ceiling (212). The ceiling (212) is a solid piece of material. In this case, the utility space (210) may be an overhead compartment. However, the utility space (210) and the passenger cabin (208) could be separated by a floor (214) of the passenger cabin (208). In this case, the utility space (210) may be a below-decks storage space.

In the specific example of FIG. 2, the utility space (210) and the passenger cabin (208) are separated by the ceiling (212). Thus, in this example, the utility space (210) is an overhead compartment.

The ceiling (212) may be of varying height relative to the floor (214) of the passenger cabin (208). In other words, the passenger cabin (208) does not have a uniform cross section across one or both of the length and width of the vehicle. In a specific example, the ceiling (212) may include an inset area (216). The inset area (216) may partially or fully impinge on the space occupied by the utility space (210). Thus, the ceiling (212) may be shaped non-uniformly in order to provide for the inset area (216).

In an embodiment, one or more overhead storage bins (218) are connected to the ceiling (212). The storage bins (218) extend into the passenger cabin (208), relative to the inset area (216). For example, the storage bins (218) may be partially or fully disposed inside the inset area (216), or may be simply accessible from the inset area (216).

The vehicle (200) also includes one or more devices (220) connected to the ceiling (212) within or on the inset area (216). The devices (220) thus could include device A (220A) and device B (220B). The devices (220) may be more or fewer in number.

Each of the devices (220) includes a corresponding rotating reflector (222). The corresponding rotating reflector (222) is a reflector that is configured to reflect ultraviolet light (and thus, for example, could be the inner shell (108) of FIG. 1 or the combination of the reflector (100) in FIG. 1). The term "corresponding rotating reflector (222)" refers to individual ones of rotating reflectors for different devices. Thus, the corresponding rotating reflector (222) may refer to individual rotating reflectors in either or both the device A (220A) and the device B (220B). In other words, the term "corresponding rotating reflector (222)" means that each of the devices (220) has its own individual rotating reflector. Some or all the reflectors (e.g., device A (220A) and/or device B (220B)) could be stationary or fixed with zero rotation.

Each of the devices (220) also includes a corresponding ultraviolet lamp (224). The corresponding ultraviolet lamp (224) is a light source configured to emit ultraviolet light. The term "corresponding ultraviolet lamp (224)" refers to individual ones of ultraviolet lamps for different devices. Thus, the corresponding ultraviolet lamp (224) may refer to individual ultraviolet lamps in either or both the device A (220A) and the device B (220B). In other words, the term "corresponding ultraviolet lamp (224)" means that each of the devices (220) has its own ultraviolet lamp.

In an embodiment, the corresponding ultraviolet lamp (224) is fixed relative to the fuselage (202). Thus, for example, the corresponding ultraviolet lamp (224) remains fixed in place as the corresponding rotating reflector (222) rotates, thereby reflecting ultraviolet light in different directions in the vehicle (200). However, in other embodiments, the corresponding ultraviolet lamp (224) could rotate or move in some other manner as the corresponding rotating reflector (222) rotates.

Figure 10:
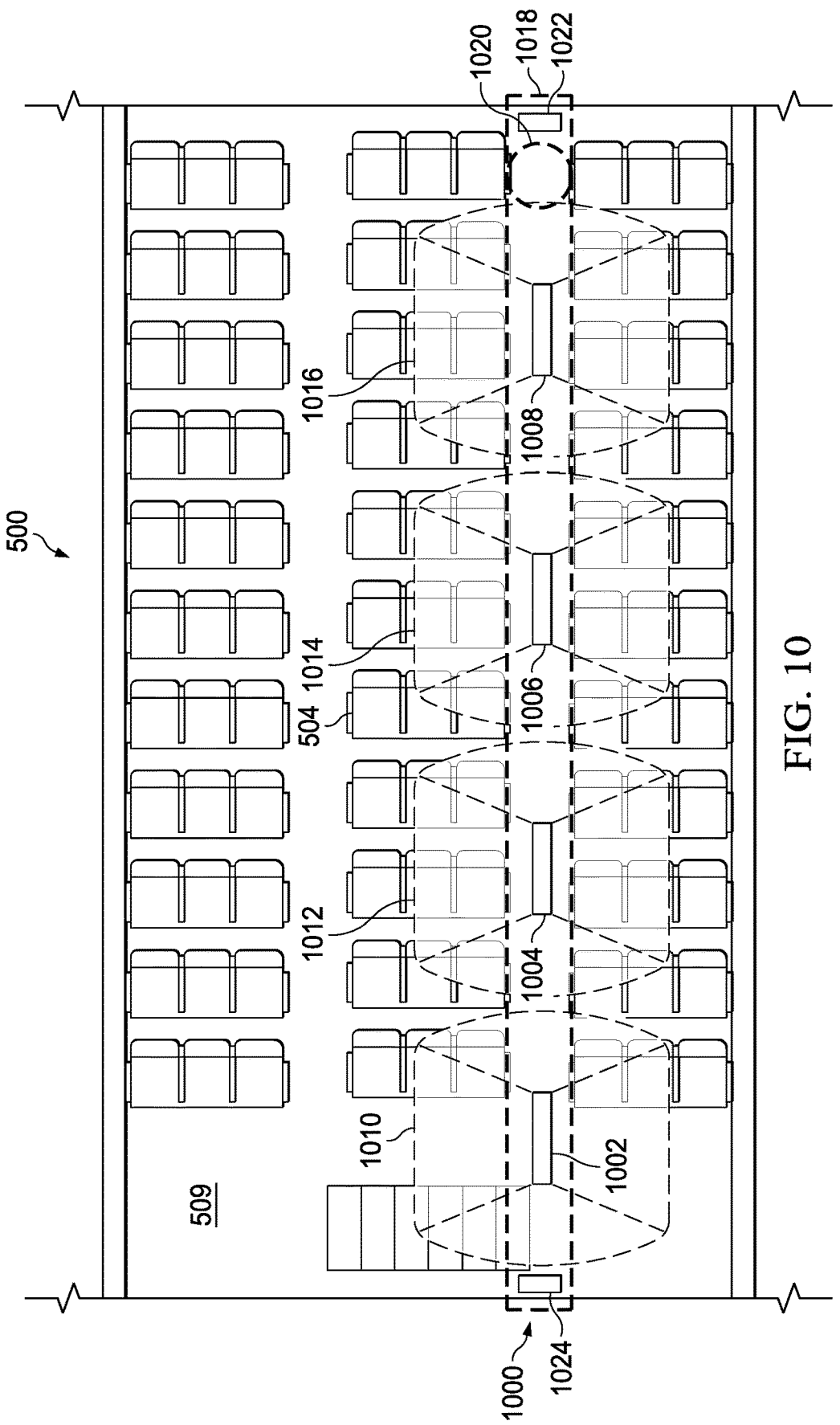
FIG. 10 shows an arrangement of multiple rotatable ultraviolet lamps within the aircraft of FIG. 4, in accordance with one or more embodiments.

In an embodiment, the devices (220) are arranged in series longitudinally end-to-end. For example, the device A (220A) and the device B (220B) may be arranged longitudinally with respect to each other relative on the ceiling (212) to the passenger cabin (208). An example of this arrangement is shown in FIG. 10.

The vehicle (200) of FIG. 2 may be varied. For example, the passenger cabin (208) may be characterized as having a sidewall (226). The sidewall (226) may be the inside portion of the outer skin (204), or may be an interior wall or separator within the passenger cabin (208).

A second ultraviolet lamp (228) may be connected to the sidewall (226). The second ultraviolet lamp (228) could also be connected to the ceiling (212) or to a ceiling junction (230) of the vehicle (200). The ceiling junction (230) is an area at or near an intersection of the ceiling (212) and the sidewall (226). The term "near" means that, in this particular embodiment, the ceiling junction (230) is closer to the ceiling (212) than to the floor (214). In any case, the second ultraviolet lamp (228) is pointed at the sidewall (226) of the passenger cabin (208). In this manner, portions of the sidewall (226) having an insufficient light path to the devices (220) can still be illuminated by a sufficient flux of ultraviolet light. The terms "insufficient" and "sufficient" refer to an amount of ultraviolet light flux deemed acceptable to accomplish a pre-specified, measurable degree of viral sterilization.

The vehicle (200) may include other features. For example, the vehicle (200) may also include a chair (232) connected to the floor (214) of the passenger cabin (208). Note that the chair (232) could also be attached to the sidewall (226) or even the ceiling (212) in other embodiments. In any case, in the example of FIG. 2, a third ultraviolet lamp (234) is connected to at least one of the chair (232) and the floor (214). The third ultraviolet lamp (234) is pointed at the ceiling (212).

For example, the third ultraviolet lamp (234) could be disposed in the pocket of an arm rest of the chair (232). At sterilization time, the third ultraviolet lamp (234) is exposed by opening a cover (or by some other means) and then the third ultraviolet lamp (234) will direct ultraviolet light upwardly towards the ceiling (212). In this manner, the ceiling (212) may be illuminated by a sufficient ultraviolet light flux.

However, the third ultraviolet lamp (234) could also be disposed underneath the chair (232). Thus, the third ultraviolet lamp (234) could point at a floor (214) or an underside portion of the chair (232).

In the alternative, or possibly in addition to the third ultraviolet lamp (234), a fourth ultraviolet lamp (236) may be connected to one of the chair (232) and/or the floor (214). The fourth ultraviolet lamp (236) points underneath the chair (232). The term "underneath" means either pointing upwardly at an underside of the fourth ultraviolet lamp (236) or downwardly towards the floor (214), or a combination of both. Note that it is possible for both the third ultraviolet lamp (234) and the fourth ultraviolet lamp (236) to be present, but in some embodiments, only one or the other of the third ultraviolet lamp (234) and the fourth ultraviolet lamp (236) are present.

Figure 5:
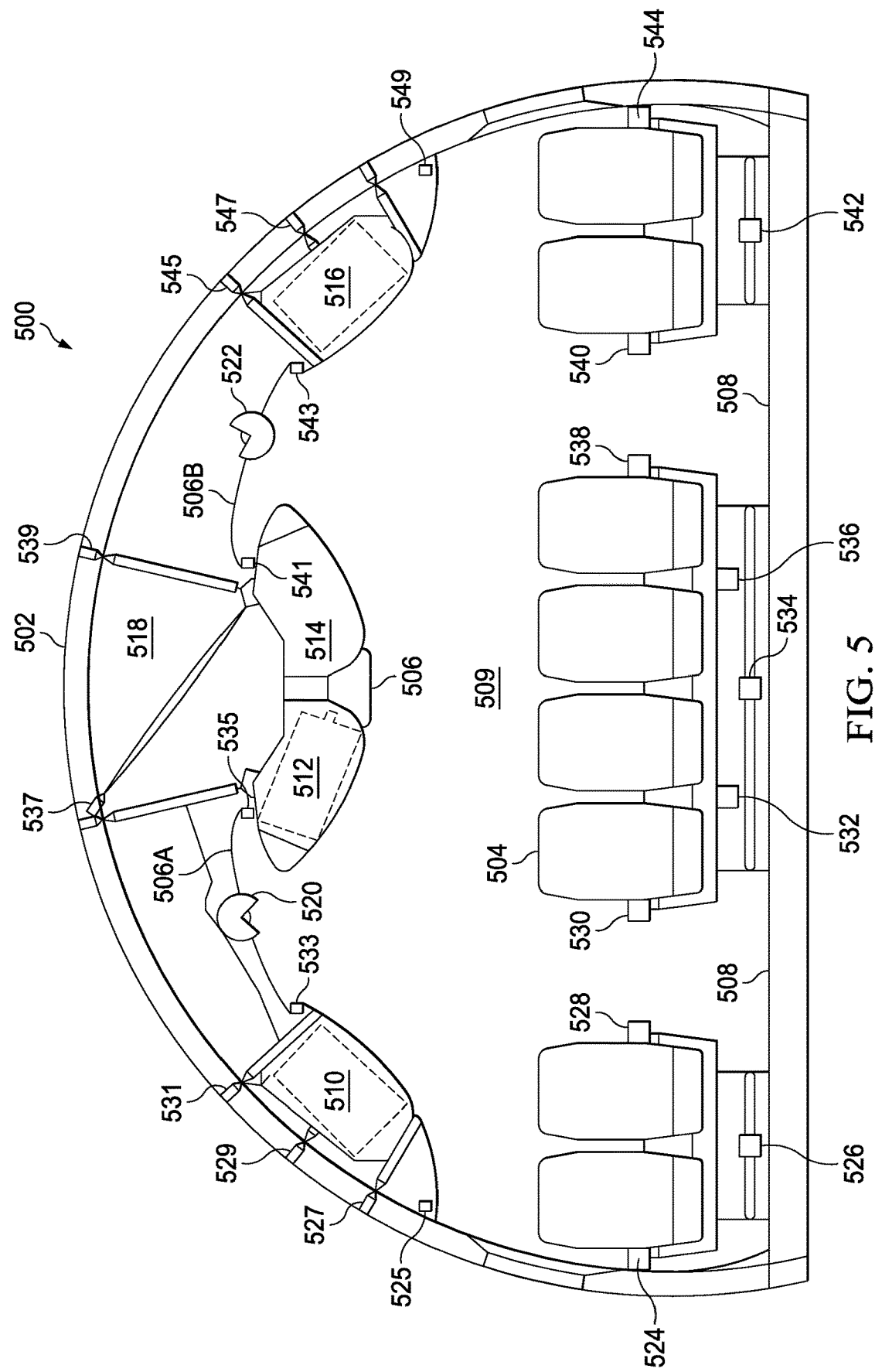
FIG. 5 shows an interior of an aircraft having an anti-viral ultraviolet light sterilization system, in accordance with one or more embodiments.

In an embodiment, one or more of the devices (220) and/or one or more of the second ultraviolet lamp (228), the third ultraviolet lamp (234), and the fourth ultraviolet lamp (236) could be similar to the reflector (100) described with respect to FIG. 1. Thus, for example, any of the lamps (e.g., the second ultraviolet lamp (228), the third ultraviolet lamp (234), and the fourth ultraviolet lamp (236)) or the devices (220) may include the various components described with respect to FIG. 1. One particular embodiment specifically contemplates that the devices (220) are multiple devices of the reflector (100) of FIG. 1, and the various ultraviolet lamps are fixed ultraviolet lamps attached to various portions of the passenger cabin (208). An example of the passenger cabin (208) is shown in FIG. 5.

In any case, the arrangement of the devices (220) and/or the other ultraviolet lamps described in FIG. 2 is selected to ensure that a pre-determined amount of ultraviolet light flux illuminates all desired spaces, nooks, and crannies within the interior (206) of the vehicle (200). Thus, the arrangement of the components of FIG. 2 allow for a desired degree of viral sterilization the interior (206) of the vehicle (200).

While FIG. 1 and FIG. 2 show configurations of components, other configurations may be used without departing from the scope of the one or more embodiments. For example, various components may be combined to create a single component. As another example, the functionality performed by a single component may be performed by two or more components.

Figure 3:
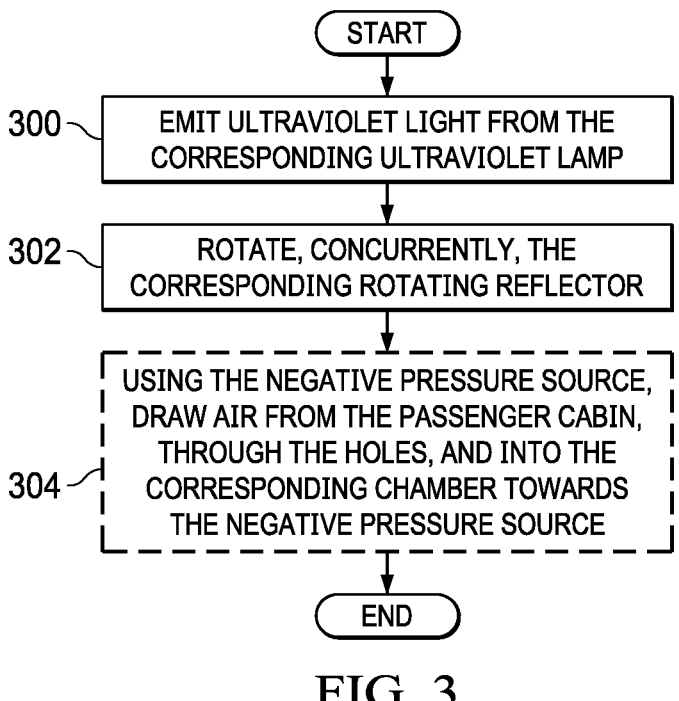
FIG. 3 shows a flowchart of a method, in accordance with one or more embodiments.

FIG. 3 shows a flowchart of a method, in accordance with one or more embodiments. The method of FIG. 3 may be accomplished in the vehicle (200) of FIG. 2. Thus, the method of FIG. 3 may be characterized as a method of sterilizing a vehicle having the parts and components described with respect to FIG. 2. The method of FIG. 3 may be characterized as a method of sterilizing a vehicle, and specifically as a method of sterilizing the vehicle (200) of FIG. 2.

At step 300, ultraviolet light is emitted from the corresponding ultraviolet lamp. Ultraviolet light may be emitted by providing electrical power to an ultraviolet light bulb or light fixture, which then converts the electrical energy into ultraviolet electromagnetic radiation. The ultraviolet light may be projected in all directions, but is reflected off of the reflector. Thus, to increase the efficiency of sterilization, the ultraviolet light initially radiating away from the target area is reflected back into the target area.

For improved sterilization efficiency, the ultraviolet light emitted may be UVC light (UVC stands for ultraviolet-C). UVC light is in the range of 200 nanometers to 265 nanometers. However, more energetic VUV (vacuum UV) light in the range of 100 nanometers to 280 nanometers could also be emitted. Thus, VUV light at 222 nanometers could be emitted. UVA (ultraviolet light-A) in the range of 315 to 400 nanometers or UVB (ultraviolet light-B) in the range of 280 to 315 nanometers could also be emitted, through preferably if UVA or UVB light is used, then the exposure time of surfaces to the ultraviolet light is increased, relative to the use of UVC light or VUV light.

At step 302, the corresponding rotating reflector is rotated, concurrently with emitting the ultraviolet light at step 300. Rotating allows the maximum ultraviolet flux emitted by the ultraviolet lamp to be directed onto a wide range of surfaces. Rotating may include rotating back and forth, rotating up to and even through 360 degrees or greater, or rotating in some pattern over time.

In the case of the vehicle (200) of FIG. 2, when the ultraviolet lamp is connected to the ceiling, rotation of the map through 360 degrees and beyond ensures that the desired amount of ultraviolet flux illuminates as many surfaces within the passenger cabin as possible (including cargo bins for use by passengers), but also to reach surfaces within the utility space above the ceiling of the passenger cabin. While the ultraviolet light may sweep through different locations at different times, by rotating through 360 degrees, fewer total ultraviolet lamps are needed to achieve ultraviolet light flux coverage over a desired number of areas.

The method of FIG. 3 may be varied. For example, the vehicle may include a negative pressure source in fluid communication with the corresponding chamber within the reflector. In this case, at step 304, the method may also include using the negative pressure source to draw air from the passenger cabin through the holes and into the corresponding chamber towards the negative pressure source. The drawn air may be vented to the outside of the vehicle, or may be stored in a waste receptacle, or may be filtered and then vented, or some combination thereof.

Drawing the air through the chamber has several beneficial effects. For example, ultraviolet lamps, especially in the VUC or UVC energy ranges, can produce ozone. Ozone, also known as trioxygen, is a molecule composed of three oxygen atoms with a chemical formula of "$O_3$". Ozone is a pale blue gas with a distinctively pungent smell. Ozone is an oxidant (i.e., can be reactive with certain other substances, including biological matter), and in concentrations above approximately 0.1 parts per million (ppm) ozone may be considered above environmental tolerances.

Drawing air through the chamber will also draw ozone through the chamber. In this manner, the amount of ozone within the passenger cabin may be ensured to stay below environmental tolerances.

Additionally, drawing air through the chamber may have other beneficial effects. For example, along with the drawn air, certain other waste products can be removed from the vehicle, such as but not limited to dust, particulates, microbes, inactivated viruses, etc.

While the various steps in the flowchart of FIG. 3 are presented and described sequentially, one of ordinary skill will appreciate that some or all of the steps may be executed in different orders, may be combined or omitted, and some or all of the steps may be executed in parallel. Thus, the one or more embodiments are not necessarily limited by the examples provided herein.

Figure 4:
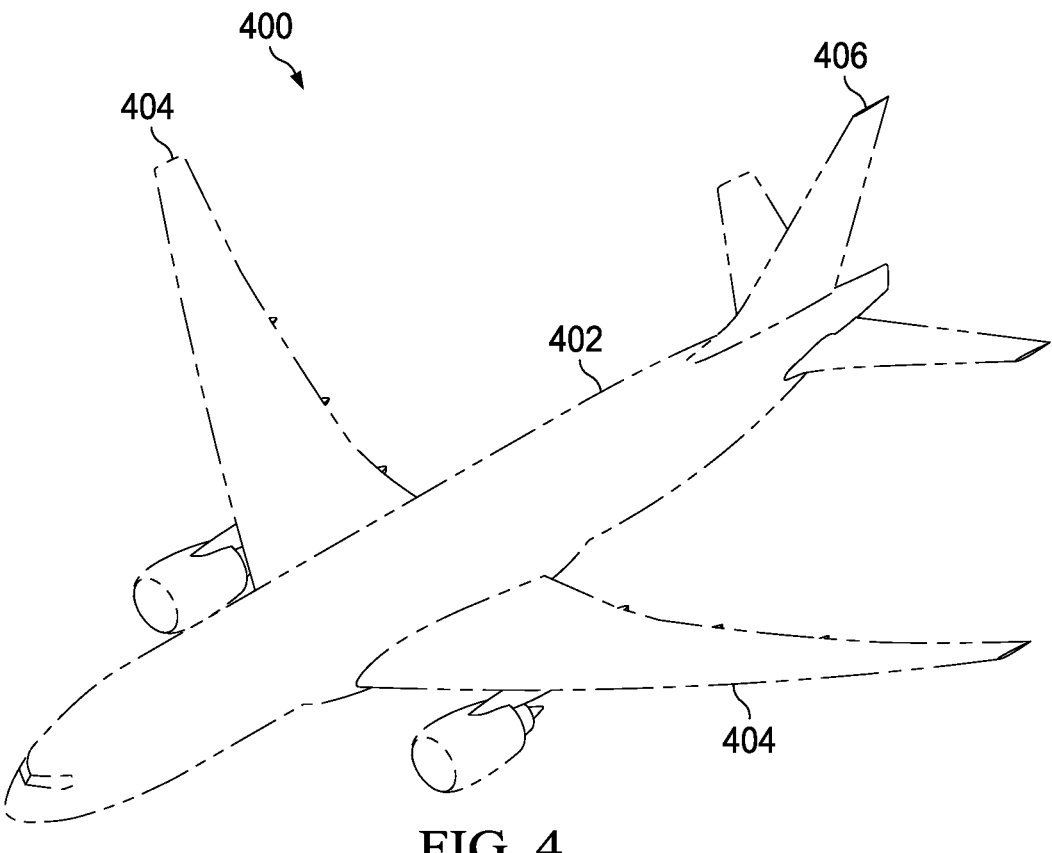
FIG. 4 shows an aircraft, in accordance with one or more embodiments.

FIG. 4 through FIG. 10 present a specific example of the devices and techniques described above with respect to FIG. 1 through FIG. 3. The following example is for explanatory purposes only and not intended to limit the scope of the one or more embodiments. In particular, FIG. 4 shows an aircraft, in accordance with one or more embodiments. FIG. 5 shows an interior of an aircraft having an anti-viral ultraviolet light sterilization system, in accordance with one or more embodiments. FIG. 6, FIG. 7, FIG. 8, and FIG. 9 show details of a rotatable ultraviolet lamp, in accordance with one or more embodiments. FIG. 10 shows an arrangement of multiple rotatable ultraviolet lamps within the aircraft of FIG. 4, in accordance with one or more embodiments.

Turning first to FIG. 4, the aircraft (400) includes a fuselage (402), at least one wing (404) and a tail (406). The aircraft (400) is an example of the vehicle (200) of FIG. 2 in which the method shown in FIG. 3 may be implemented.

Attention is now turned to FIG. 5. The aircraft (500) FIG. 5 shows a cross section of the aircraft (400) shown in FIG. 4. The fuselage (502) thus corresponds to the fuselage (402) of FIG. 4.

The aircraft (500) includes a number of additional features including a number of chairs, such as chair (504). The aircraft (500) also includes a ceiling (506), a floor (508), and a passenger cabin (509) defined between the floor (508) and the ceiling (506). Several luggage bins are connected to the ceiling (506), including luggage bin A (510), luggage bin B (512), luggage bin C (514), and luggage bin D (516). A utility space (518) is defined between the ceiling (506) and the fuselage (502), above the ceiling (506) relative to the floor (508). Insets, such as first inset (506A) and second inset (506B) may be disposed in the ceiling (506). Note that the exteriors of the various luggage compartments may effectively form part of the ceiling (506), or may be considered to be connected in additional insets in the ceiling (506).

A sterilization system is included in the aircraft (500). The sterilization system is a set of one or more ultraviolet lamps, possibly in conjunction with other connected devices that direct ultraviolet light emitted by the ultraviolet lamps.

For example, the sterilization system includes a first reflector (520) at one side of passenger cabin and a second reflector (522) at the other side. The first reflector (520) and the second reflector (522) may be the reflector (100) shown in FIG. 1, or may be as described with respect to FIG. 6 through FIG. 10.

The sterilization system may include potentially one or more of possibly many additional ultraviolet lamps spaced in locations throughout the aircraft (500) so that a desired degree of ultraviolet light flux reaches all desired spaces within the aircraft (500).

Thus, for example, UV lamp A (524), UV lamp B (526), UV lamp C (528), UV lamp D (530), UV lamp E (532), UV lamp F (534), UV lamp G (536), UV lamp H (538), UV lamp I (540), UV lamp J (542), and UV lamp K (544) may be disposed with respect to the chairs (such as chair (504)) in the aircraft (500). The term "disposed with respect to the chairs" refers to a specific orientation of the UV lamps with respect to one or more of the chairs. For example, some of the UV lamps may be attached to the armrests in the chairs, such as UV lamp A (524), UV lamp C (528), UV lamp D (530), UV lamp H (538), UV lamp I (540), and UV lamp K (544). In these cases, the UV lamps may be disposed in insets in the armrests. At sterilization time, the maps may be activated, possibly in conjunction with removing or pulling back covers over the UV maps in the armrests. However, some of the UV lamps may be placed in other locations with respect to the chairs, such as the UV lamp B (526), the UV lamp E (532), and the UV lamp G (536), which are placed on the undersides of the seats of the chairs. Such UV lamps may be pointed underneath the chairs and in particular aimed downwardly towards the floor (508). In another example, such as for UV lamp J (542), the UV lamp may be placed on some other supporting structure for the chair. The UV lamp J (542) is still considered pointing underneath the chair, but may be pointing either upwardly, downwardly, or from side to side relative to the floor (508). Still other UV lamps may be connected to the floor (508) and pointed upwardly, such as UV lamp F (534). In this case, while still being considered to point underneath the chair, the UV light can sterilize the undersides of the chairs.

The sterilization system may include still other UV lamps placed elsewhere within the passenger cabin (509) and/or the utility space (518). For example, various UV lamps may be placed on the near the ceiling (506), such as UV lamp 1 (525), UV lamp 5 (533), UV lamp 6 (535), UV lamp 9 (541), UV lamp 10 (543), and UV lamp 13 (549). In this particular example, the UV lamp 1 (525) and the UV lamp 13 (549) are located at junctures between the sidewalls of the fuselage (502). Additional UV lamps can be placed in the utility space (518) and directed to shine UV light on various places within the utility space (518), such as UV lamp 2 (527), UV lamp 3 (529), UV lamp 4 (531), UV lamp 7 (537), UV lamp 8 (539), UV lamp 11 (545), and UV lamp 12 (547).

FIG. 6, FIG. 7, FIG. 8, and FIG. 9 show details of a rotatable ultraviolet lamp reflector assembly, in accordance with one or more embodiments. FIG. 6 through FIG. 9 thus share common reference numerals referring to common objects. The reflector (600) shown in FIG. 6 is an example of the reflector (100) described with respect to FIG. 1 through FIG. 3. Thus, terms used with respect to FIG. 6 may be similar to terms used with respect to FIG. 1. Thus, FIG. 6 shows a particular exemplary implementation of the reflector (100) shown in FIG. 1. Note also that the reflector (600) may also be used in the aircraft (400) of FIG. 4, and may specifically be either of the first reflector (520) or the second reflector (522) described with respect to FIG. 5.

The reflector (600) includes an outer shell (602) connected to an inner shell (604). The outer shell (602) is opaque to UV light and to visible light. The outside of the outer shell (602) may have a decorative finish that matches a cabin of a vehicle or room, to improve the ascetic appearance of the device relative to the vehicle or room. The outer shell (602) has a first longitudinal axis (617) that defines a central axis of the outer shell (602). The outer shell (602) has a first arcuate shape, as shown in FIG. 6. The first arcuate shape is circular in FIG. 6, though the first arcuate shape may be elliptical, parabolic, or complex. A complex shape is a mix of different shapes, possibly with discontinuous components.

The inner shell (604) is reflective, at least on one side (605), to ultraviolet light. The inner shell (604) has holes, such as hole (606), that penetrate through the material that forms the inner shell (604). Note that in some embodiments, the hole (606) need not be present.

The inner shell (604) has a second longitudinal axis (616) that defines a central axis of the inner shell (604). In some embodiments, the second longitudinal axis (616) may be colinear with the first longitudinal axis (617), though the two axes need not be colinear or even parallel in some cases. In the embodiment shown in FIG. 6, the first longitudinal axis (617) is parallel to the second longitudinal axis (616).

The inner shell (604) has a second arcuate shape, as shown in FIG. 6. The second arcuate shape is parabolic in FIG. 6, though the second arcuate shape may be elliptical, parabolic, or complex. A complex shape is a mix of different shapes, possibly with discontinuous components.

A difference in the arcuate shapes of the outer shell (602) and the inner shell (604) forms a chamber (608) defined between the outer shell (602) and the inner shell (604). As described below, the chamber (608) may be used to draw air and ozone out of the surrounding area, into the chamber (608), and through an outlet (622) of a negative pressure source (620).

An ultraviolet light source (610) is disposed on a reflective side of the inner shell (604), such that the ultraviolet light source (610) is opposite the outer shell (602) relative to the inner shell (604). The ultraviolet light source (610) may be located at a focal length of the inner shell (604). In the example shown in FIG. 6, the ultraviolet light source (610) is a tubular ultraviolet light source disposed along the second longitudinal axis (616).

A number of additional axes may be used to define the arrangement of components of the reflector (600). For example, the outer shell (602) and the inner shell (604) are joined together at a first longitudinal length (612) and a second longitudinal length (614). Finally, dashed lines (618) indicate the outer portion of the UV light envelope generated by the reflector (600) when the ultraviolet light source (610) is activated.

In an embodiment, a negative pressure source (620) is operably connected to the reflector (600). "Operably connected" means that the negative pressure source (620) has a fluid line that connects to the chamber (608). In this manner, the negative pressure source (620) can be actuated to draw air and ozone (generated by operation of the ultraviolet light source (610)) through the holes (606), into the chamber (608), and towards the negative pressure source (620). An outlet (622) is provided so that the air and ozone drawn towards the negative pressure source (620) may be transferred as exhaust elsewhere, such as outside of a vehicle or room.

Note that the outlet (622) may be located elsewhere, such as in the outer shell (608), elsewhere with respect to the negative pressure source (620), or in still some other location. The negative pressure source (620) may be disposed in some other location relative to the reflector (600). The negative pressure source (620) may be some other type of negative pressure source. The negative pressure source (620) may be replaced with some other device, such as a positive pressure source (e.g., a fan or a blower). Thus, the examples described with respect to FIG. 6 do not necessarily limit other examples described herein.

In an embodiment, an actuator (624) is connected to the outer shell (602), though in other embodiments, the actuator (624) is connected to the inner shell (604) or to both the inner shell (604) and the outer shell (602). The actuator (624) is a motor configured to rotate a drive shaft (626) connected to the motor. In turn, the drive shaft (626) is connected to the outer shell (602) (and/or the inner shell (604)). Thus, when the actuator (624) rotates the drive shaft (626) around a third longitudinal axis (628) of the drive shaft (626), the combination of the outer shell (602) and the inner shell (604) (which may be referred-to as an "assembly") likewise will rotate. In this manner, the assembly (i.e., the combination of the outer shell (602) and the inner shell (604)) rotates around the ultraviolet light source (610), which in this embodiment remains stationary. The third longitudinal axis (628) may be parallel to the first longitudinal axis (616) and/or the second longitudinal axis (617), or may have some other orientation with respect to the other axes. Note that in some embodiments, the ultraviolet light source (610) may also rotate as the combination of the outer shell (602) and the inner shell (604) rotates. In this embodiment, all the axis (616, 617, 628) are colinear and are located at the focal point of the inner shell (604).

Attention is now turned to FIG. 7. FIG. 7 shows how ultraviolet light is emitted from the ultraviolet light source (610). In particular, the reflector (600) reflects the ultraviolet light from the ultraviolet light source (610) as the reflector (600) rotates, as indicated by arrows (700). Because the inner shell (604) of the reflector (600) has an ellipsoidal shape, the ultraviolet light tends to be focused along a first light path envelope (702). Some light, however, escapes from other portions of the opening that is defined between the first longitudinal length (612) and the second longitudinal length (614) (seen in FIG. 6). Thus, some ultraviolet light will be projected within a second light path envelope (704). The first light path envelope (702) is narrower than the second light path envelope (704), and contains more ultraviolet light flux than the second light path envelope (704), resulting in effective sanitization sweep along the path of the first light path envelope (702).

Figure 8:
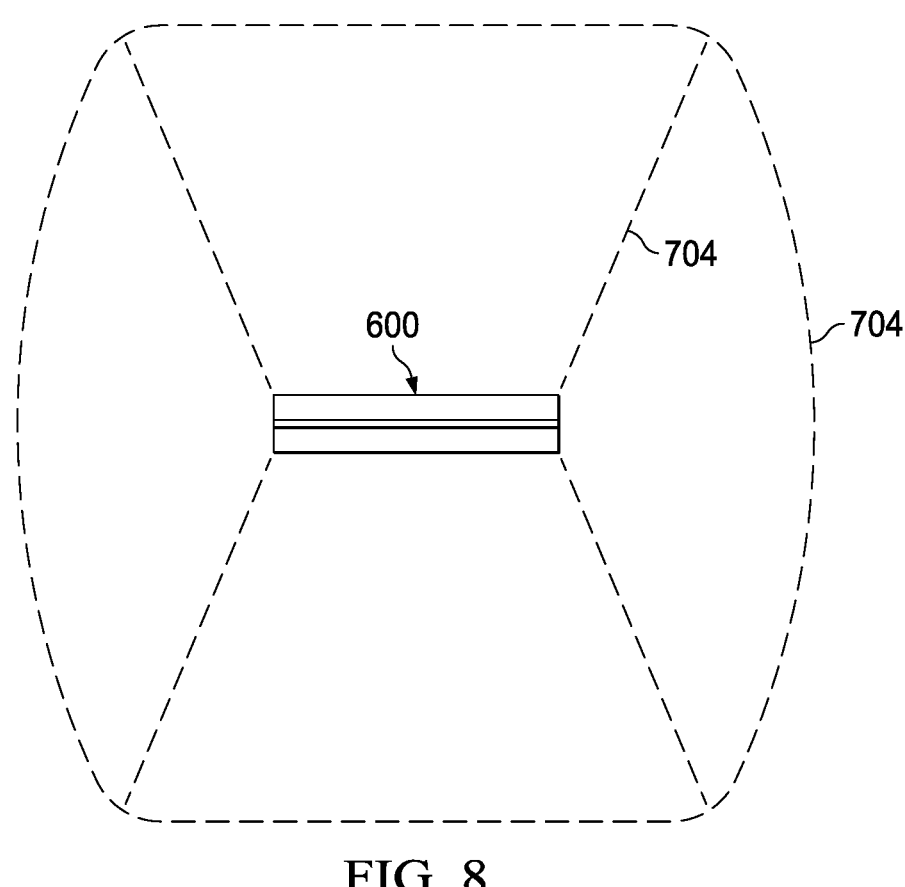
Figure 9:
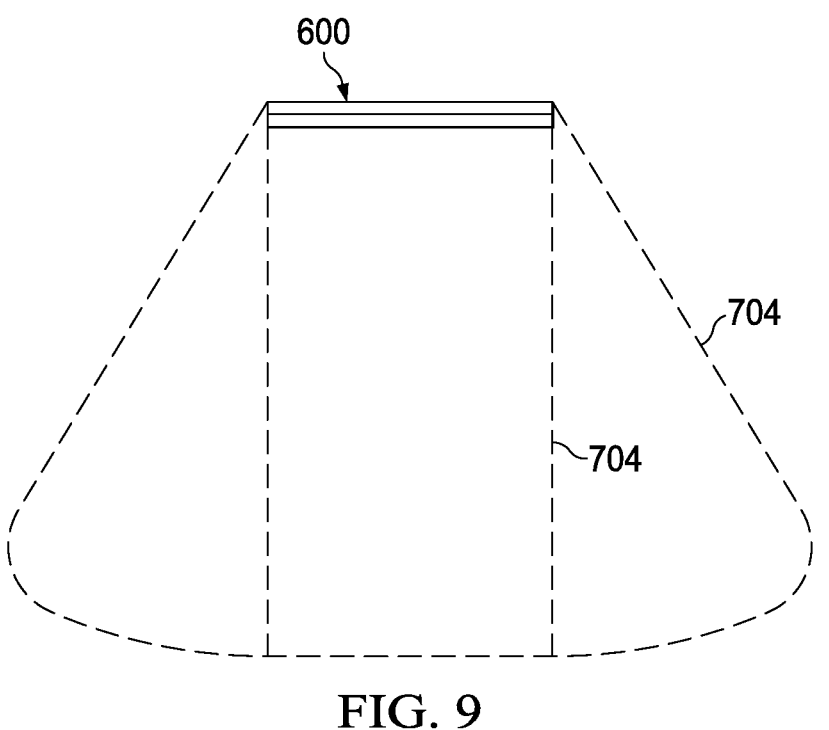

FIG. 8 shows an overhead view of the reflector (600). The second light path envelope (704) is shown as an umbrella-like shape that is projected into the page. Similarly, FIG. 9 shows another perspective, showing a side view of the reflector (600). The second light path envelope (704) is shown in the umbrella-like shape that is projected out of the page, but from the side so that the longitudinal edges of the second light path envelope (704) are in the page.

FIG. 10 shows an arrangement of reflectors in an aircraft, such as the aircraft (500) of FIG. 5. FIG. 5 and FIG. 10 share some reference numerals, which refer to similar objects.

FIG. 10 shows the passenger cabin (509) of the aircraft (500) and a number of chairs, such as chair (504), arranged in the passenger cabin (509). A series (1000) of reflectors are connected to the ceiling (not shown) of the aircraft. The series of (1000) of reflectors have holes through which air and ozone may be drawn. The series (1000) of reflectors includes reflector A (1002), reflector B (1004), reflector C (1006), and reflector D (1008) arranged longitudinally in series. In the embodiment of FIG. 10, the series (1000) of reflectors all lie along the same longitudinal axis, just above one passenger isle or path. However, the series (1000) of reflectors could be staggered or otherwise lie along different longitudinal axes with respect to the aircraft (500).

The reflectors in the series (1000) each produce an envelope of UV flux. Again, the term "UV" means "ultraviolet". Thus, for example, reflector A (1002) produces UV envelope A (1010), reflector B (1004) produces UV envelope B (1012), reflector C (1006) produces UV envelope C (1014), and reflector D (1008) produces UV envelope D (1016). Each UV envelope is configured to bathe a portion of the passenger cabin (509) and the chairs with sufficient UV flux to sterilize or inactivate viruses.

Additionally, FIG. 10 shows a fluid line (1018) connected to each of the reflectors in the series (1000). The fluid line (1018) in turn is connected to a negative pressure source (1020). As described with respect to FIG. 3, the negative pressure source (1020) may draw air from the passenger cabin (509), into the fluid line (1018), and towards the negative pressure source (1020). In this manner, at least some of the ozone created by the UV generation may be drawn out of the passenger cabin (509). A vent (1022) is connected to the fluid line (1018). The vent (1022) allows the drawn air and ozone to either be vented into the outside air, or to be placed into a receptacle for storage.

Note that additional series of reflectors may be present in the aircraft (500). However, only one series (1000) is shown for clarity. Furthermore, additional UV lamps may be located inside the aircraft (500), as described with respect to FIG. 5. Still other variations are possible, such as additional vents, additional fluid lines, or additional negative pressure sources within any one of the series of reflectors. In another example, one or more power sources, such as power source (1024), may be available to power the UV light sources and/or the mechanical actuators that rotate the reflectors.

Thus, the one or more embodiments are not necessarily limited to the example of FIG. 10.

Figure 11:
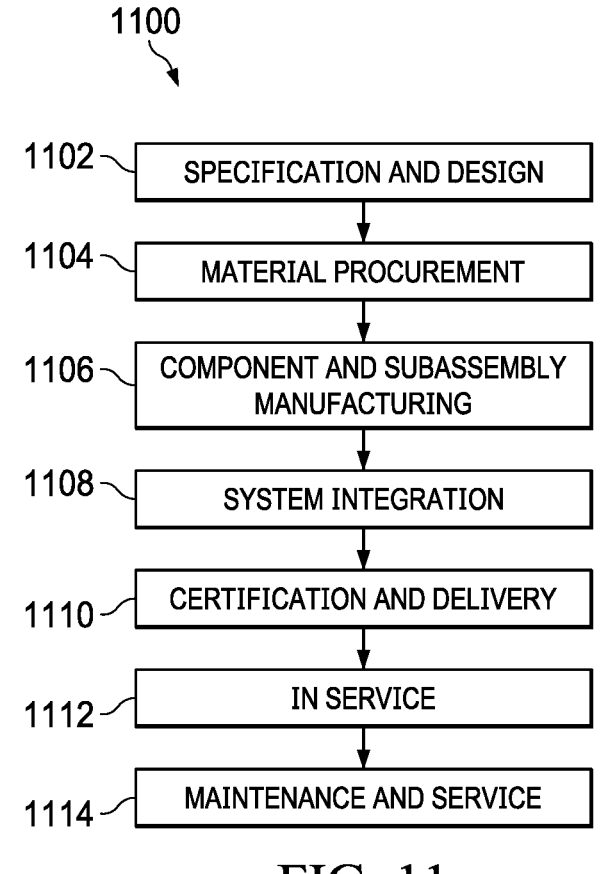
FIG. 11 is an exemplary aircraft manufacturing and service method, in accordance with one or more embodiments.
Figure 12:
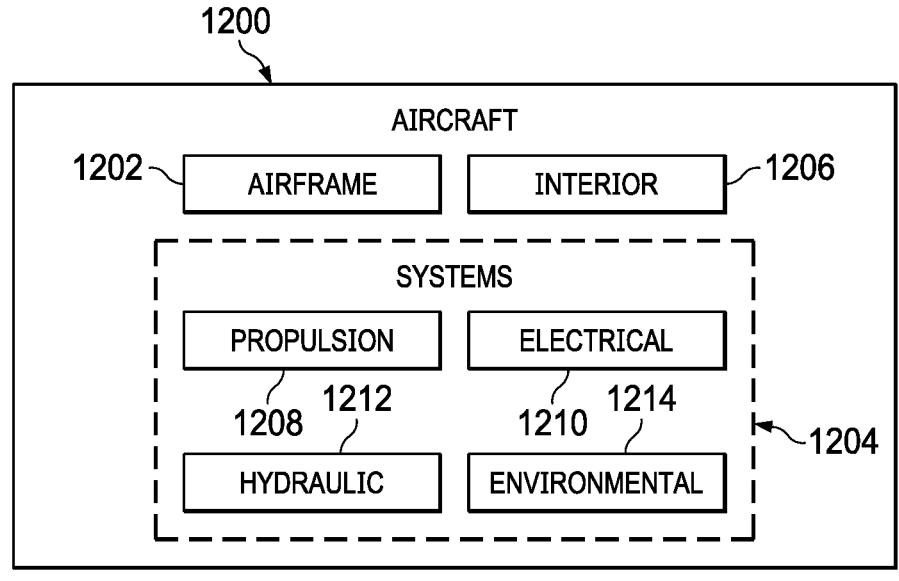
FIG. 12 is another example of an aircraft, in accordance with one or more embodiments.

Turning to FIG. 11, during pre-production, the exemplary aircraft manufacturing and service method (1100) may include a specification and design (1102) of the aircraft (1200) in FIG. 12 and a material procurement (1104) for the aircraft (1200). During production, the component and subassembly manufacturing (1106) and system integration (1108) of the aircraft (1200) in FIG. 12 takes place. Thereafter, the aircraft (1200) in FIG. 12 may go through certification and delivery (1110) in order to be placed in service (1112). While in service by a customer, the aircraft (1200) in FIG. 12 is scheduled for routine maintenance and service (1114), which may include modification, reconfiguration, refurbishment, and other maintenance or service.

Each of the processes of the aircraft manufacturing and service method (1100) may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, leasing company, military entity, service organization, and so on.

With reference now to FIG. 12, an illustration of an aircraft (1200) is depicted in which an advantageous embodiment may be implemented. In this example, the aircraft (1200) is produced by the aircraft manufacturing and service method (1100) in FIG. 11. The aircraft (1200) may include airframe (1202) with systems (1204) and an interior (1206). Examples of systems (1204) include one or more of a propulsion system (1208), an electrical system (1210), a hydraulic system (1212), and an environmental system (1214). Any number of other systems may be included.

Although an aerospace example is shown, different advantageous embodiments may be applied to other industries, such as the automotive industry. Thus, for example, the aircraft (1200) may be replaced by an automobile or other vehicle or object in one or more embodiments.

The apparatus and methods embodied herein may be employed during any one or more of the stages of the aircraft manufacturing and service method (1100) in FIG. 11. For example, components or subassemblies produced in the component and subassembly manufacturing (1106) in FIG. 11 may be fabricated or manufactured in a manner similar to components or subassemblies produced while the aircraft (1200) is in service (1112) in FIG. 11.

Also, one or more apparatus embodiments, method embodiments, or a combination thereof may be utilized during production stages, such as the component and subassembly manufacturing (1106) and system integration (1108) in FIG. 11, for example, by substantially expediting the assembly of or reducing the cost of the aircraft (1200) Similarly, one or more of apparatus embodiments, method embodiments, or a combination thereof may be utilized while the aircraft (1200) is in service (1112) or during maintenance and service (1114) in FIG. 11.

One or more embodiments also include a lighting assembly comprising:

an outer shell coaxially aligned with an inner shell such that the outer shell shrouds the inner shell and forms a chamber therebetween; the assembly configured to rotate to direct light from a light source housed within the inner shell. Wherein the lighting assembly is rotatably attached to a ceiling of an aircraft. Wherein the outer shell has an arcuate shape that is different from a shape of the inner shell.

For example, one or more of the advantageous embodiments may be applied during component and subassembly manufacturing (1106) to rework inconsistencies that may be found in composite structures. As yet another example, one or more advantageous embodiments may be implemented during maintenance and service (1114) to remove or mitigate inconsistencies that may be identified. Thus, the one or more embodiments described with respect to FIG. 1 through FIG. 9 may be implemented during component and subassembly manufacturing (1106) and/or during maintenance and service (1114) to remove or mitigate inconsistencies that may be identified.

While the one or more embodiments have been described with respect to a limited number of embodiments, those skilled in the art, having benefit of this disclosure, will appreciate that other embodiments can be devised which do not depart from the scope of the one or more embodiments as disclosed herein. Accordingly, the scope of the one or more embodiments should be limited only by the attached claims.

What is claimed is:

1. A device comprising:

an outer shell having a first longitudinal axis and a first arcuate shape;

an inner shell having a second longitudinal axis, wherein the inner shell is connected longitudinally to the outer shell along a first longitudinal length and a second longitudinal length, wherein the inner shell has a second arcuate shape different than the first arcuate shape, wherein a chamber is disposed between the outer shell and the inner shell, and wherein the chamber is defined by a difference between the first arcuate shape and the second arcuate shape;

an ultraviolet light source disposed along the second longitudinal axis; and an actuator connected to at least one of the outer shell and the inner shell, wherein the actuator is configured to rotate the outer shell and the inner shell together about the ultraviolet light source.

2. The device of claim 1, further comprising:

a negative pressure source in fluid communication with the chamber.

3. The device of claim 1, wherein the second arcuate shape is elliptical, and the first arcuate shape is circular.

4. The device of claim 1, wherein a plurality of holes penetrate through the inner shell.

5. The device of claim 1, wherein the outer shell comprises a composite material and the inner shell comprises aluminum alloy.

6. The device of claim 1, wherein the ultraviolet light source comprises a tube along a length of the inner shell.

7. The device of claim 1, wherein the inner shell has an outer surface that reflects ultraviolet light, and wherein the outer shell is opaque to ultraviolet light and to visible light.

* * * * *